(12) United States Patent
Hubert-Brierre et al.

(10) Patent No.: US 10,525,265 B2
(45) Date of Patent: Jan. 7, 2020

(54) IMPULSE NOISE MANAGEMENT

(71) Applicant: Cochlear Limited, Macquarie University, NSW (AU)

(72) Inventors: Florent Maxime Hubert-Brierre, Mechelen (BE); Thomas Leroux, Mougins (BE)

(73) Assignee: Cochlear Limited, Macquarie University, NSW (AU)

( * ) Notice: Subject to any disclaimer, the term of this patent is extended or adjusted under 35 U.S.C. 154(b) by 427 days.

(21) Appl. No.: 14/962,785

(22) Filed: Dec. 8, 2015

(65) Prior Publication Data
US 2016/0165362 A1 Jun. 9, 2016

Related U.S. Application Data

(60) Provisional application No. 62/089,544, filed on Dec. 9, 2014.

(51) Int. Cl.
*H04R 25/00* (2006.01)
*A61N 1/36* (2006.01)

(52) U.S. Cl.
CPC ........ *A61N 1/36036* (2017.08); *H04R 25/606* (2013.01); *H04R 2225/67* (2013.01)

(58) Field of Classification Search
CPC .............. H04R 25/606; H04R 2225/67; H04R 2460/13
USPC .......... 381/320, 317, 321, 312; 600/25, 559, 600/586; 607/57, 55; 3/320, 317, 321, 3/312
See application file for complete search history.

(56) References Cited

U.S. PATENT DOCUMENTS

| | | | | |
|---|---|---|---|---|
| 4,816,125 A | * | 3/1989 | Muller | H04R 17/00 204/192.18 |
| 4,998,179 A | * | 3/1991 | Grantham | G01L 9/0073 361/283.4 |
| 5,280,524 A | * | 1/1994 | Norris | H04M 1/05 379/388.02 |
| 5,814,095 A | * | 9/1998 | Muller | A61N 1/36032 607/56 |
| 5,999,632 A | * | 12/1999 | Leysieffer | A61F 2/18 181/130 |
| 6,084,516 A | * | 7/2000 | Yasushi | A61B 5/0002 340/4.14 |
| 6,198,971 B1 | * | 3/2001 | Leysieffer | A61N 1/36032 607/55 |

(Continued)

OTHER PUBLICATIONS

International Search Report and Written Opinion for PCT/IB2015/051316, dated Apr. 29, 2015.

(Continued)

*Primary Examiner* — Phylesha Dabney
(74) *Attorney, Agent, or Firm* — Piloff Passino & Cosenza LLP; Martin J. Cosenza

(57) ABSTRACT

A microphone system including a first sensor configured to output a first signal based on an ambient sound relative to a recipient of the system, a second sensor configured to output a second signal corresponding to a noise reference, and first signal processing circuitry configured to process the first signal based on the second signal and output a third signal based on the processed first signal, wherein the system is configured to limit a gain of the third signal based on the presence of impulsive energy in the second signal.

27 Claims, 9 Drawing Sheets

(56) References Cited

U.S. PATENT DOCUMENTS

| | | | |
|---|---|---|---|
| 6,330,339 B1* | 12/2001 | Ishige | H04R 25/502 |
| | | | 381/312 |
| 6,342,035 B1* | 1/2002 | Kroll | H04R 25/606 |
| | | | 600/25 |
| 6,394,947 B1* | 5/2002 | Leysieffer | H04R 25/505 |
| | | | 600/25 |
| 6,629,923 B2* | 10/2003 | Leysieffer | A61N 1/36032 |
| | | | 600/25 |
| 6,707,920 B2 | 3/2004 | Miller | |
| 6,888,949 B1 | 5/2005 | Vanden Berghe et al. | |
| 7,853,031 B2 | 12/2010 | Hamacher | |
| 8,014,871 B2 | 9/2011 | Dalton et al. | |
| 8,096,937 B2 | 1/2012 | Miller, III | |
| 8,472,654 B2 | 6/2013 | Miller, III | |
| 2001/0031996 A1* | 10/2001 | Leysieffer | A61N 1/36032 |
| | | | 607/57 |
| 2002/0138115 A1* | 9/2002 | Baumann | A61N 1/36032 |
| | | | 607/57 |
| 2003/0171787 A1 | 9/2003 | Money et al. | |
| 2004/0234089 A1* | 11/2004 | Rembrand | H04R 25/30 |
| | | | 381/312 |
| 2005/0101831 A1 | 5/2005 | Miller et al. | |
| 2006/0140425 A1* | 6/2006 | Berg | A61B 5/00 |
| | | | 381/312 |
| 2006/0155346 A1 | 7/2006 | Miller | |
| 2006/0183965 A1 | 8/2006 | Kasic et al. | |
| 2007/0009122 A1* | 1/2007 | Hamacher | H04R 25/453 |
| | | | 381/312 |
| 2007/0009132 A1 | 1/2007 | Miller | |
| 2007/0021647 A1 | 1/2007 | Slattery et al. | |
| 2009/0187065 A1 | 7/2009 | Basinger | |
| 2010/0317913 A1 | 12/2010 | Conn et al. | |
| 2011/0098785 A1 | 4/2011 | Mishra | |
| 2011/0178438 A1 | 7/2011 | Van Gerwen | |
| 2011/0200222 A1 | 8/2011 | Miller, III et al. | |
| 2012/0232333 A1 | 9/2012 | Miller, III | |
| 2013/0079634 A1 | 3/2013 | Kerber | |
| 2014/0012350 A1 | 1/2014 | Kasic, II et al. | |
| 2015/0256949 A1 | 9/2015 | Vanpoucke et al. | |

OTHER PUBLICATIONS

Kaibao Nie et al., "Encoding Frequency Modulation to Improve Cochlear Implant Performance in Noise", In: IEEE Transactions on Biomedical Engineering, Jan. 2005, vol. 52, Issue 1, pp. 64-73 ("http://ieeexplore.ieee.org/xpls/abs_all.jsp?arnumber=1369589").

Herman A. Jenkins et al., Speech Perception Comparisons Using an Implanted and an External Microphone in Existing Cochlear Implant Users, Otology & Neurotology, 2012, vol. 33, No. 1, Department of Otolaryngology, University of Colorado School of Medicine, Aurora, Colorado, U.S.A.

* cited by examiner

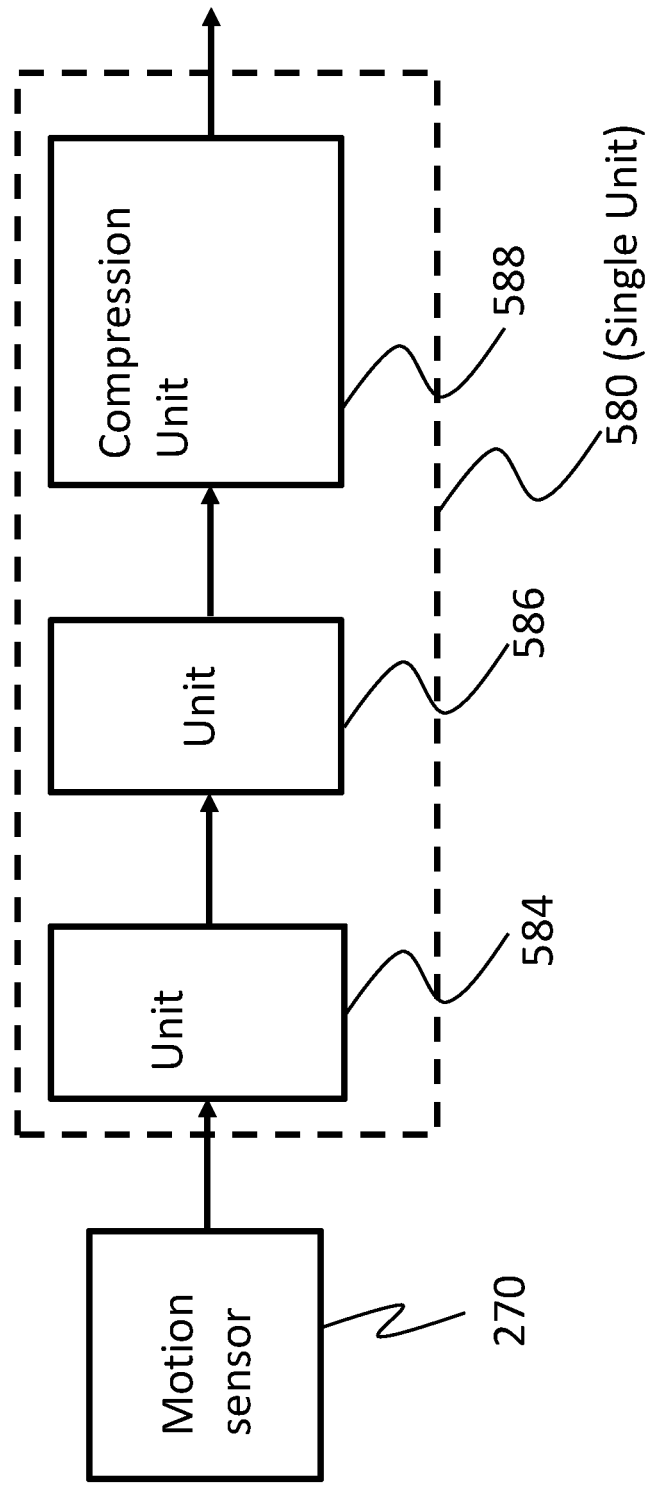

IMPULSE NOISE MANAGEMENT

CROSS-REFERENCE TO RELATED APPLICATIONS

This application claims priority to Provisional U.S. Patent Application No. 62/089,544, entitled IMPULSE NOISE MANAGEMENT, filed on Dec. 9, 2014, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal, or on the outer ear, to amplify a sound received by the outer ear of the recipient. This amplified sound reaches the cochlea causing motion of the perilymph and stimulation of the auditory nerve.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound.

Another type of hearing prosthesis uses an actuator to mechanically vibrate the ossicular chain, whereby an amplified signal can reach the cochlea. This type of hearing prosthesis can have utility for both conductive losses and sensorineural loss, depending on the level of hearing loss.

SUMMARY

In accordance with an exemplary embodiment, there is a system, comprising a microphone system, comprising a first sensor configured to output a first signal based on an ambient sound relative to a recipient of the system, a second sensor configured to output a second signal corresponding to a noise reference, and first signal processing circuitry configured to process the first signal based on the second signal and output a third signal based on the processed first signal, wherein the system is configured to limit a gain (broadband or frequency dependent) of the third signal based on the presence of impulsive energy in the second signal.

In accordance with another exemplary embodiment, there is a subcutaneous microphone system, comprising a first implantable transducer configured to transduce energy from an ambient signal and body noise, a second implantable transducer configured to transduce energy from body noise, a first signal processing path, and a second signal processing path, wherein an output of the first implantable transducer and an output of the second implantable transducer are inputs to the first signal processing path, the output of the second implantable transducer is an input to the second signal processing path, and the microphone system is configured to vary gain applied to the first signal processing path based on a characteristic of a signal of the second signal processing path.

In accordance with another exemplary embodiment, there is a method, comprising outputting first signals at a first location within a recipient, while the recipient is verbally silent, that are based at least in part on first body noise and first ambient noise, both of which are conducted through tissue of the recipient, subsequently outputting second signals at the first location within the recipient, while the recipient is verbally silent, that are based at least in part on second body noise and second ambient noise, both of which are conducted through tissue of the recipient, determining that an impulsive energy level of the first body noise is at least one of at or below a threshold level or that an impulsive energy level of the second body noise is at least one of at or above the threshold level, processing the outputted signals by applying a first broadband gain regime to the first signals and applying a second broadband gain regime to the second signals different from the first broadband gain regime, and evoking respective hearing percepts based on the processed outputted signals.

In accordance with another embodiment, there is a hearing prosthesis, comprising an adaptive signal processing sub-system, and a gain compression sub-system configured to be reactive to body noise, wherein the gain compression sub-system is independent of the adaptive signal processing sub-system and is configured to compress gain of the microphone system independently of the adaptive signal processing sub-system.

BRIEF DESCRIPTION OF THE DRAWINGS

Embodiments of the present invention are described below with reference to the attached drawings, in which:

FIG. 5 is a functional diagram of an exemplary signal path according to an exemplary embodiment;

DETAILED DESCRIPTION

Figure 1:
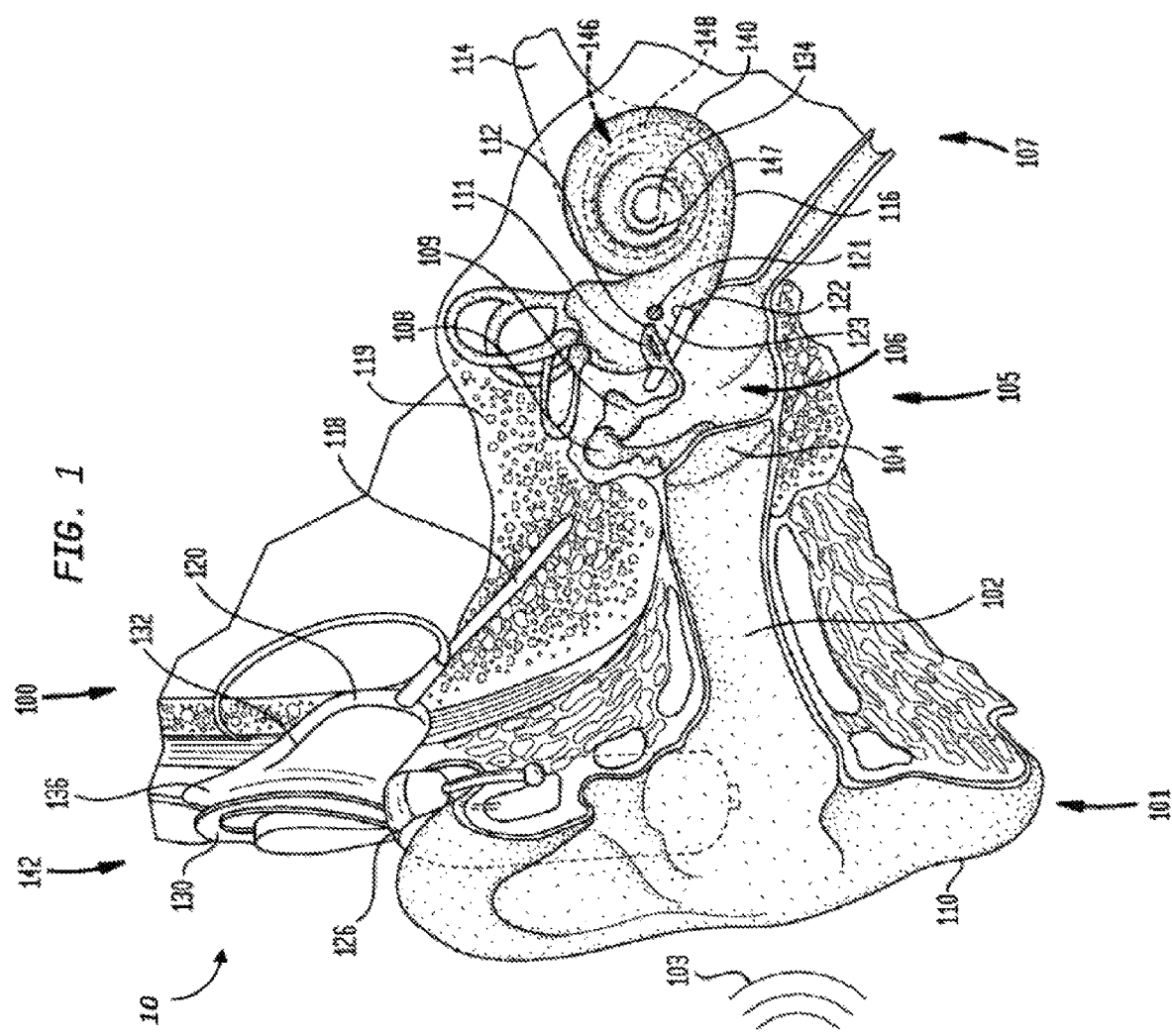
FIG. 1 is a perspective view of an exemplary hearing prosthesis in which at least some of the teachings detailed herein are applicable.

FIG. 1 is a perspective view of a totally implantable cochlear implant, referred to as cochlear implant 100, implanted in a recipient, to which some embodiments detailed herein and/or variations thereof are applicable. The totally implantable cochlear implant 100 is part of a system 10 that can include external components, in some embodiments, as will be detailed below. It is noted that the teachings detailed herein are applicable, in at least some embodiments, to any type of hearing prosthesis having an implantable microphone.

It is noted that in alternate embodiments, the teachings detailed herein and/or variations thereof can be applicable to other types of hearing prostheses, such as, for example, bone conduction devices (e.g., active transcutaneous bone conduction devices), Direct Acoustic Cochlear Implant (DACI), etc. Embodiments can include any type of hearing prosthesis that can utilize the teachings detailed herein and/or variations thereof. It is further noted that in some embodiments, the teachings detailed herein and/or variations thereof can be utilized by other types of prostheses beyond hearing prostheses.

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant, where the implanted cochlear implant includes a battery that is recharged by the power provided from the external device 142. In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement. Some additional details associated with the implantable microphone assembly 137 will be detailed below.

Main implantable component 120 further includes a stimulator unit (not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

As noted above, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source can comprise, for example, a rechargeable battery. During operation of cochlear implant 100, the power stored by the power source is distributed to the various other implanted components as needed. The power source may be located in main implantable component 120, or disposed in a separate implanted location.

It is noted that the teachings detailed herein and/or variations thereof can be utilized with a non-totally implantable prosthesis. That is, in an alternate embodiment of the cochlear implant 100, the cochlear implant 100 is a traditional hearing prosthesis.

In some exemplary embodiments, a signal sent to the stimulator of the cochlear implant can be derived from an external microphone, in which case the system is called a semi-implantable device, or from an implanted microphone, which then refers to a fully implantable device. DACIs and other types of implants can also use an implanted microphone, and thus are also fully implantable devices. Fully implantable devices can have utility by presenting improved cosmesis, can have an improved immunity to certain noises (e.g., wind noise), can present few opportunities for loss or damage, and can at least sometimes be more resistant to clogging by debris or water, etc. DACIs can have utilitarian value by keeping the ear canal open, which can reduce the possibility of infection of the ear canal, which otherwise is humid, often impacted with cerumen (earwax), and irritated by the required tight fit of a non-implanted hearing aid.

Implanted microphones can detect pressure. In at least some embodiments, implanted microphones are configured to detect air pressure, which is subsequently transmitted through the tissue to the microphone, such as to a diaphragm or membrane of the microphone. Implanted microphones can detect other pressures presented to their surface, which can be undesirable in certain circumstances. One type of pressure which can represent an impairment to the performance of an implanted microphone is pressure due to acceleration. In some embodiments, such acceleration can have a deleterious effect on a hearing prosthesis if it is in the desired operational frequency range of the prosthesis, typically 20 Hz to 20 kHz, although narrower ranges still give satisfactory speech intelligibility. Accelerations may arise from, for example, foot impact during walking, motion of soft tissue relative harder tissues, wear of harder tissues against each other, chewing, blowing one's nose, a grumbling stomach, laughing, and vocalization, etc.

In some embodiments, the accelerations induce pressure on the microphone, which cannot distinguish the desired pressure due to external sounds from what may be undesirable pressure due to internal vibration originating directly from the body. The accelerations can be thought of as giving rise to these pressures by virtue of the microphone being driven into the tissue. If the microphone is securely mounted on the skull, and the skull vibrates normal to its surface, the microphone diaphragm will be driven into the tissue which, due to the mass, and hence inertia of the tissue, can present a reactive force to the microphone. That reactive force divided by the area of the microphone is the pressure generated by acceleration.

In some instances, there can be utilitarian value to reducing signal outputs due to acceleration. Because the relative body-borne to air-borne pressure of an implanted microphone is typically 10-20 dB higher than that that occurs in normal hearing, body originating sounds can be louder relative to externally originating sound. Such large ratios of vibration to acoustic signals are experienced by a recipient as banging and crashing during movement, very noisy chewing, and their own voice being abnormally loud relative to other speakers. At the same time, it is noted that there is utilitarian value in some instances in avoiding the cancellation of all or part of the recipient's own voice. Complete cancellation of the recipient's own voice can result in, in some scenarios, the recipient speaking very loudly compared to other speakers. It is therefore utilitarian to reduce the ratio of vibration to acoustic signals to a level, such as a comparable level, to that found in normal hearing.

An exemplary embodiment that includes an implantable microphone assembly utilizes a motion sensor to reduce the effects of noise, including biological noise, in an output response of the implantable microphone assembly. In an exemplary embodiment, the diaphragm of the implantable microphone assembly that vibrates as a result of waves traveling through the skin of the recipient originating from an ambient sound, can be also affected by body noise and the like. To actively address non-ambient noise sources (e.g., body noise conducted through tissue of a recipient to a microphone, which in at least some embodiments is not of an energy level and/or frequency to be audible at a location away from the recipient, at least not without sound enhancement devices) of vibration of the diaphragm of the implantable microphone and thus the resulting undesired movement between the diaphragm and overlying tissue, some embodiments utilize a motion sensor to provide an output response proportional to the vibrational movement experienced by the microphone assembly. Generally, the motion sensor can be mounted anywhere such that it enables the provision of a sufficiently accurate representation of the vibration received by the implantable microphone in general, and the diaphragm of the implantable microphone in particular. The motion sensor can be part of the assembly that contains the microphone/diaphragm thereof, while in an alternate embodiment, it can be located in a separate assembly (e.g. a separate housing, etc.). In an exemplary embodiment, the motion sensor is at least partially isolated from the receipt of the ambient acoustic signals originating from an ambient sound that pass transcutaneously through the tissue located over the microphone/diaphragm of the microphone and which are received by the microphone diaphragm. In this regard, the motion sensor can provide an output response/signal that is indicative of motion (e.g., caused by vibration and/or acceleration), whereas a transducer of the microphone can generate an output response/signal that is indicative of both transcutaneously received acoustic sound and motion. Accordingly, the output response of the motion sensor can be removed from the output response of the microphone to reduce the effects of motion on the implanted hearing system.

Figure 2:
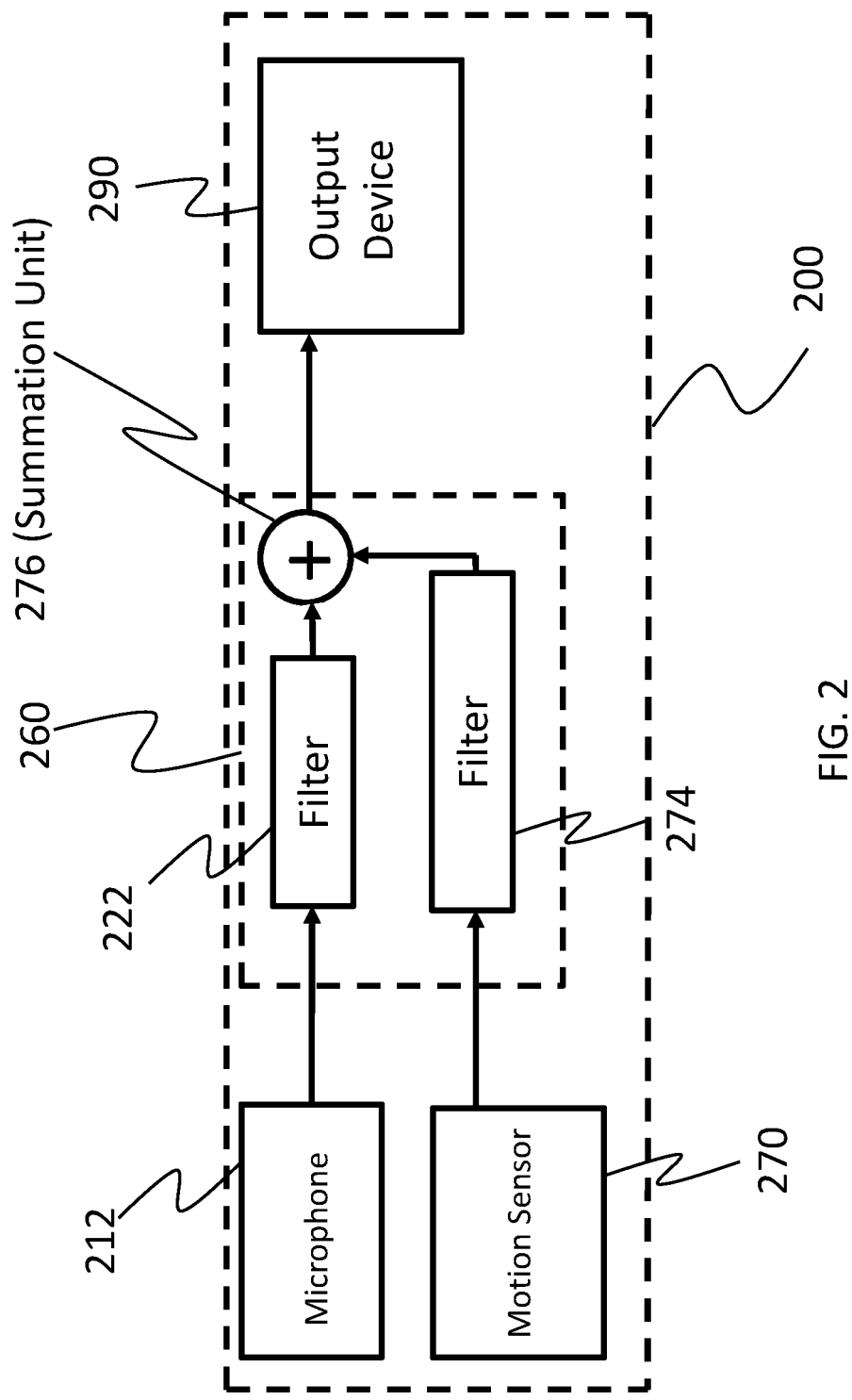
FIG. 2 schematically illustrates an implantable hearing system that incorporates an implantable microphone assembly and a motion sensor.

Accordingly, to remove noise, including biological noise (and in some instances, feedback), it is utilitarian to measure the acceleration of the microphone assembly. FIG. 2 schematically illustrates an implantable hearing system that incorporates an implantable component of a hearing prosthesis 200 including a microphone assembly having a microphone 212 and motion sensor 270 (which in some embodiments can be an accelerometer). As shown, the motion sensor 270 further includes a filter 274 (although in other embodiments, filter 274 is not present) that is utilized for matching the output response of the motion sensor 270 to the output response of the microphone 212 (where the output thereof is also filtered, in some embodiments, by filter 222). One or both of the filters 222 and 274 can be adaptive filters that adapt to changing circumstances. Of note, the diaphragm of microphone 212 is subject to desired acoustic signals (i.e., from an ambient source 103), as well as undesired signals from biological sources (e.g., vibration caused by talking, chewing, etc.) and, depending on the type of output device 290 (e.g., bone conduction vibratory apparatus, DACI actuator, and in some instances, cochlear implant electrode array) feedback from the output device 290 received by a tissue feedback loop extending from the output device 290 to the microphone 212 and the motion sensor 270. In contrast, the motion sensor 270 is at least partially isolated (which includes totally isolated) from the ambient source and is subjected to the undesired signals caused by the biological source and/or by feedback received via the feedback loop. Accordingly, the output of the motion sensor 270 corresponds to some or all of the undesired signal components of the microphone 212. However, the magnitude of the output channels (i.e., the output response of the microphone 212 and output response of the motion sensor 270) can be different and/or shifted in phase. In order to remove the undesired signal components from the microphone output response, the filter 274 and/or the system processor can be operative to filter one or both of the responses to provide scaling, phase shifting and/or frequency shaping. The output responses of the microphone 212 and motion sensor 270 are then combined by summation unit 276, which generates a net output response that has a reduced response to the undesired signals, which net output response is used to operate the output device 290.

Collectively, filters 222 and 274, the adder 276, and any control equipment used to control these components correspond a noise cancellation sub-system 260.

In order to implement a filter 274 for scaling and/or phase shifting the output response of a motion sensor 270 to remove the effects of feedback and/or biological noise from a microphone 212 output response, a system model of the relationship between the output responses of the microphone 212 and motion sensor 270 is identified/developed.

Figure 3A:
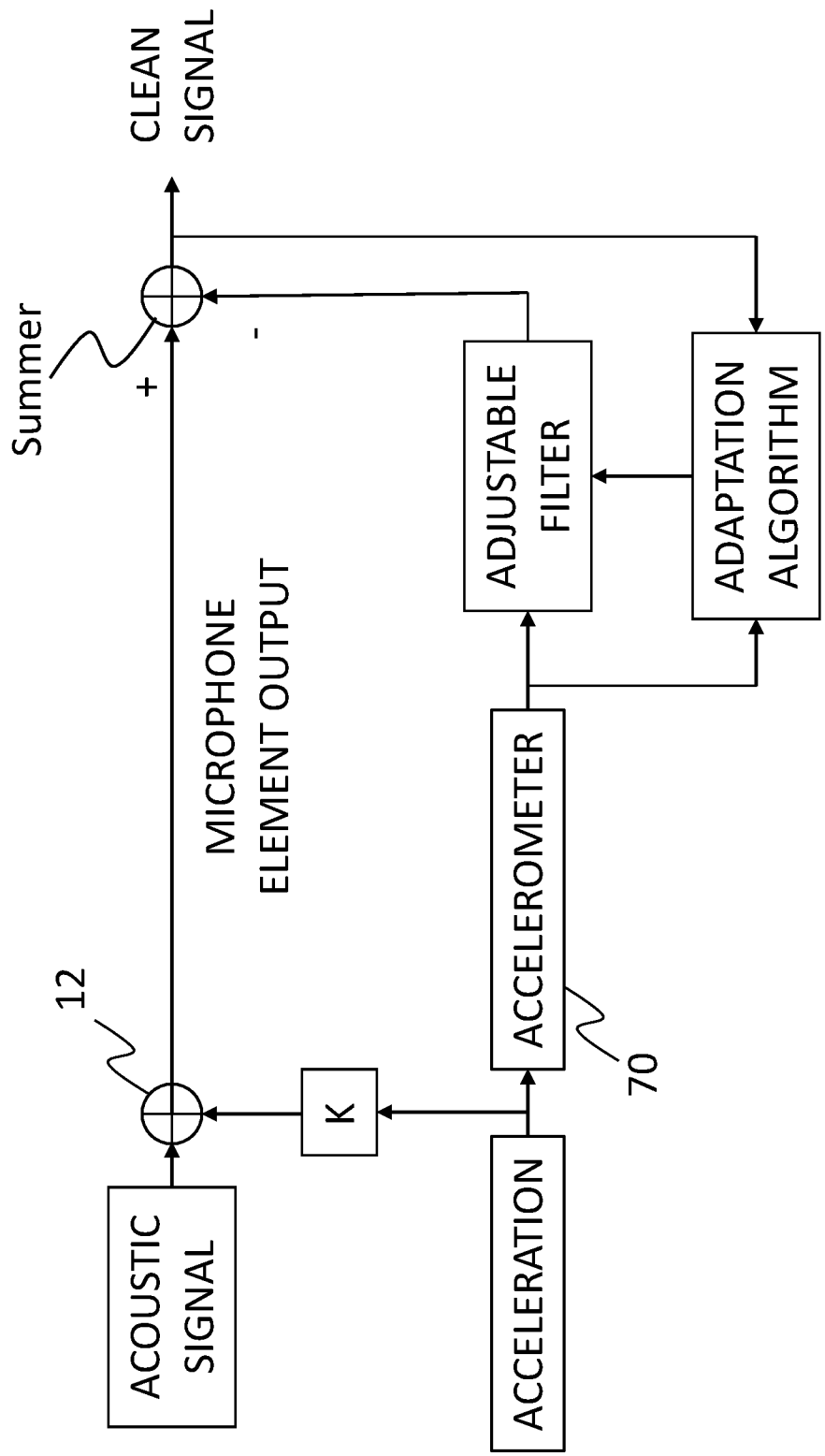
FIG. 3A functionally illustrates an exemplary use of adaptive filters.

As noted above, an exemplary embodiment utilizes adaptive filter(s) to filter out body noise and the like. More particularly, FIG. 3A functionally illustrates an exemplary use of such adaptive filters. In FIG. 3A, biological noise is modeled by the acceleration at the microphone assembly filtered through a linear process K. This signal is added to the acoustic signal at the surface of the microphone element. In this regard, the microphone 212 sums the signals. If the combination of K and the acceleration are known, the combination of the accelerometer output and the adaptive/adjustable filter can be adjusted to be K. This is then subtracted out of the microphone output. This will result in the cleansed or net audio signal with a reduced biological noise component. This net signal may then be passed to the signal processor where it can be processed by the hearing system.

Figure 3B:
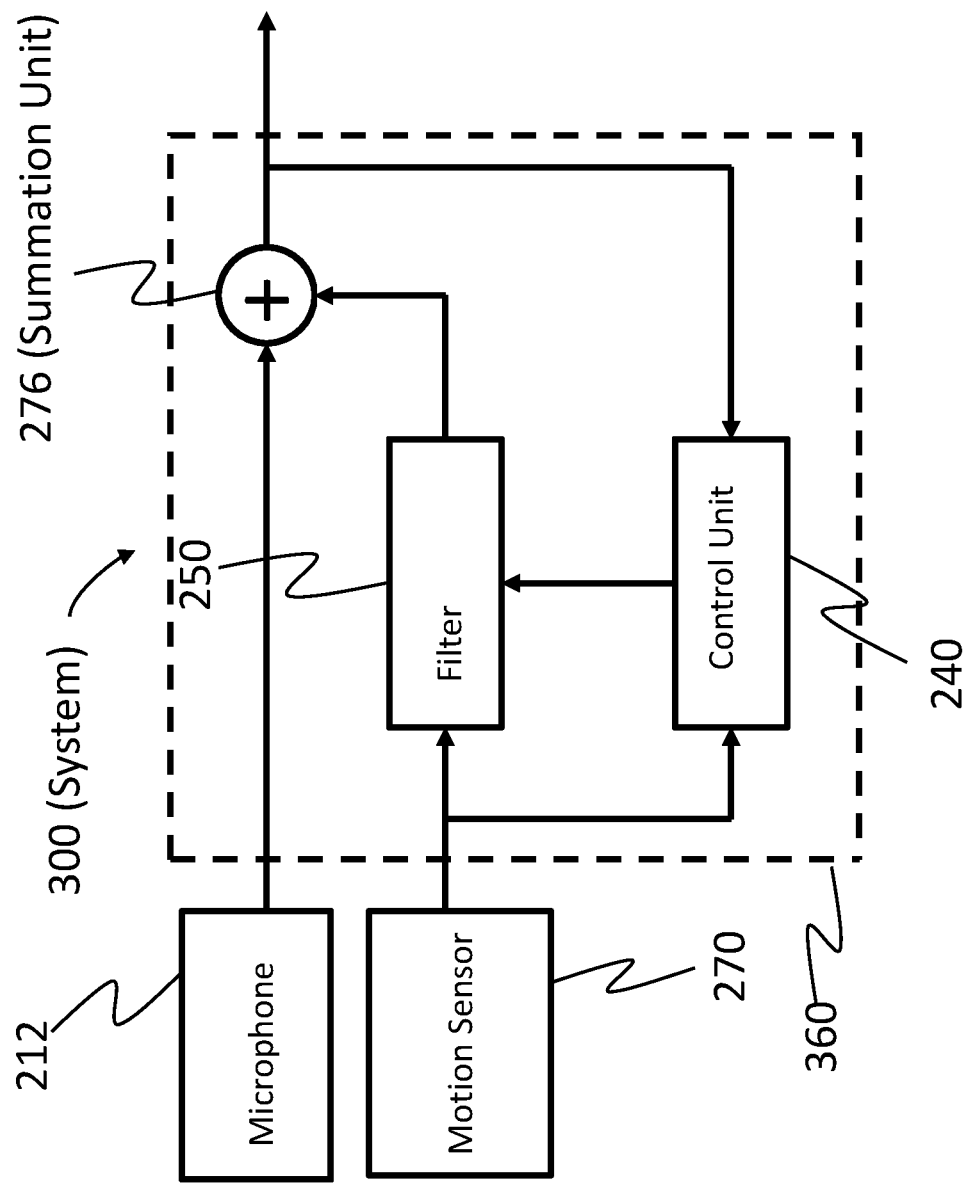
FIG. 3B functionally depicts an exemplary embodiment of a system that is usable in the hearing prosthesis of FIG. 1 that functionally operates in accordance with the schematic of FIG. 3A.

FIG. 3B functionally depicts an exemplary embodiment of a system 300 that is usable in the hearing prosthesis 10 of FIG. 1 and that functionally operates in accordance with the schematic of FIG. 3A. The system 300 includes microphone 212 and accelerometer 270. The microphone 212 is configured such that it receives signals resulting from the ambient sound, as well as biological noise/body noise, including, in at least some embodiments, signals resulting from a recipient's own voice that travel through the body via bone conduction/tissue conduction, and other own body conducted noises (e.g., noises originating from coughing, blowing one's nose, etc.). These latter signals are added at the microphone 212 to the signals resulting from ambient sound, because the microphone 212 detects both signals. Conversely, accelerometer 270 is at least partially isolated from the signals resulting from the ambient sound, and generally responds to body noise signals and/or feedback signals. The system 300 incorporates an adjustable filter apparatus 250 controlled by a control unit 240 that runs an adaptive algorithm to control the filter(s) of the adjustable filter apparatus 250. Briefly, as can be seen, the output of the adaptive filter apparatus 250, controlled by filter control unit 240, is fed to adder 276, wherein it is added to (or, more accurately, subtracted from) the output of the microphone 212, and passed on to a signal processor and/or an output device (not shown, but for example, a receiver stimulator of a cochlear implant, an actuator of a DACI, and/or an actuator (vibrator) of an active transcutaneous bone conduction device) of the system. Collectively, the adjustable filters 250, the filter control unit 240, and the adder 276 correspond to an adaptive noise cancellation sub-system 360, which can include additional components (e.g., filters in between the microphone 212 and the mixer/adder 276).

The functionality and operation of the adaptive noise cancellation sub-system 360 can be more detailed/involved than that just described. Some exemplary embodiments can utilize very advanced adaptive noise cancellation techniques. That said, in alternative embodiments, as inferred above, some systems do not utilize an adaptive noise cancellation system, and can instead utilize traditional systems. Any device, system and/or method that can enable noise cancellation sub-system 360 to operate can be utilized in at least some embodiments.

Figure 4A:
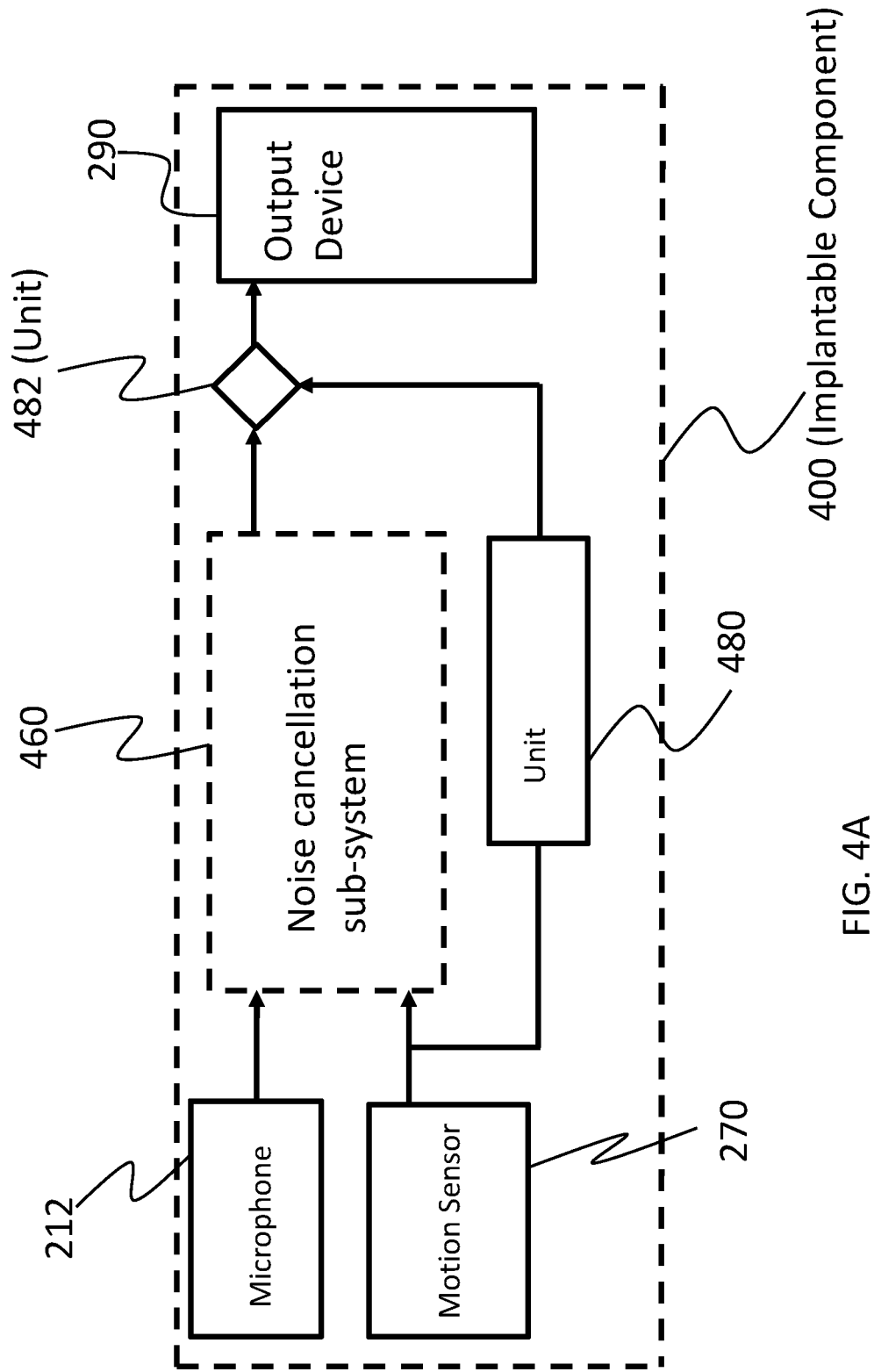
FIG. 4A is a schematic illustration of an exemplary embodiment utilizing a reference signal to identify impulsive noises according to an exemplary embodiment.

FIG. 4A presents a functional diagram of an exemplary implantable component of a hearing prosthesis including an impulse noise management system, which in an exemplary embodiment, is a broadband impulse noise management system, and in another exemplary embodiment, is a frequency dependent noise management system. Specifically, FIG. 4A depicts implantable component 400 of a hearing prosthesis, which includes a noise cancellation sub-system 460, which can correspond to that of sub-system 360 or 260 detailed above, or any other noise cancellation sub-system that can enable the teachings detailed herein and/or variations thereof to be practiced. The implantable component 400 includes the microphone 212 and motion sensor 270 detailed above with respect to FIG. 2. Microphone 212 corresponds to an implantable transducer configured to transduce energy from an acoustic signal (e.g., ambient sound impinging upon skin of the recipient and causing energy to reach the microphone 212) and body noise. Motion sensor 270 corresponds an implantable transducer configured to transduce energy originating from body noise. In the embodiment of FIG. 4A, motion sensor 270 is at least partially isolated from energy originating from the acoustic signal.

The outputs of these transducers are inputted into the noise cancellation sub-system 460 as can be seen. Also, as can be seen in FIG. 4A, the outputs of the motion sensor 270 are also provided to a unit 480. In an exemplary embodiment, unit 480 identifies a broadband compression regime having utilitarian value based on an analysis of the signal outputted by motion sensor 270 (additional details of which are provided below). (That said, in alternative embodiments, the compression regime is a frequency dependent compression regime that is narrower than a broadband compression regime. It is noted that the following will be described in terms of a broadband compression and broadband impulse noise, but alternative embodiments can be practiced with a frequency dependent regimes and frequency specific impulse noises, unless otherwise specified.) Based on this identified broadband compression regime, the signal to be provided to the output device 290 (e.g., the output from the noise cancellation sub-system 460) is subjected to broadband compression based on the identified broadband compression regime, as exemplified by the output from unit 480 being applied to unit 482, where the output from sub-system 460 is also applied thereto. The output from unit 480 is a signal that subjects the signal to be used to control output device 290 to a compressed broadband gain (compressed relative to that which would otherwise be the case, as detailed below). In an exemplary embodiment, unit 480 is a unit configured to analyze the outputted signal outputted from motion sensor 270 to identify a broadband compression regime having utilitarian value.

As noted above, FIG. 4A is a functional schematic. It is intended to represent a configuration where a control signal is outputted from unit 480 that controls unit 482 to apply broadband compression to the output from the sub-system 460. Any device, system, and/or method that can enable the signal that is provided to the device 290, or, more generally, the signal that is used to operate device 290, to have broadband compression based on the teachings detailed herein and/or variations thereof can be utilized in at least some embodiments. Indeed, referring now to FIG. 4B, which depicts an implantable component of a hearing prostheses 400, it is noted that in an alternate embodiment, the output from unit 480 is fed directly to the noise cancellation sub-system 460. In such an exemplary embodiment, the noise cancellation subsystem 460 is configured to receive the output of the unit 480, and output a signal having broadband compression to output device 290.

Figure 4B:
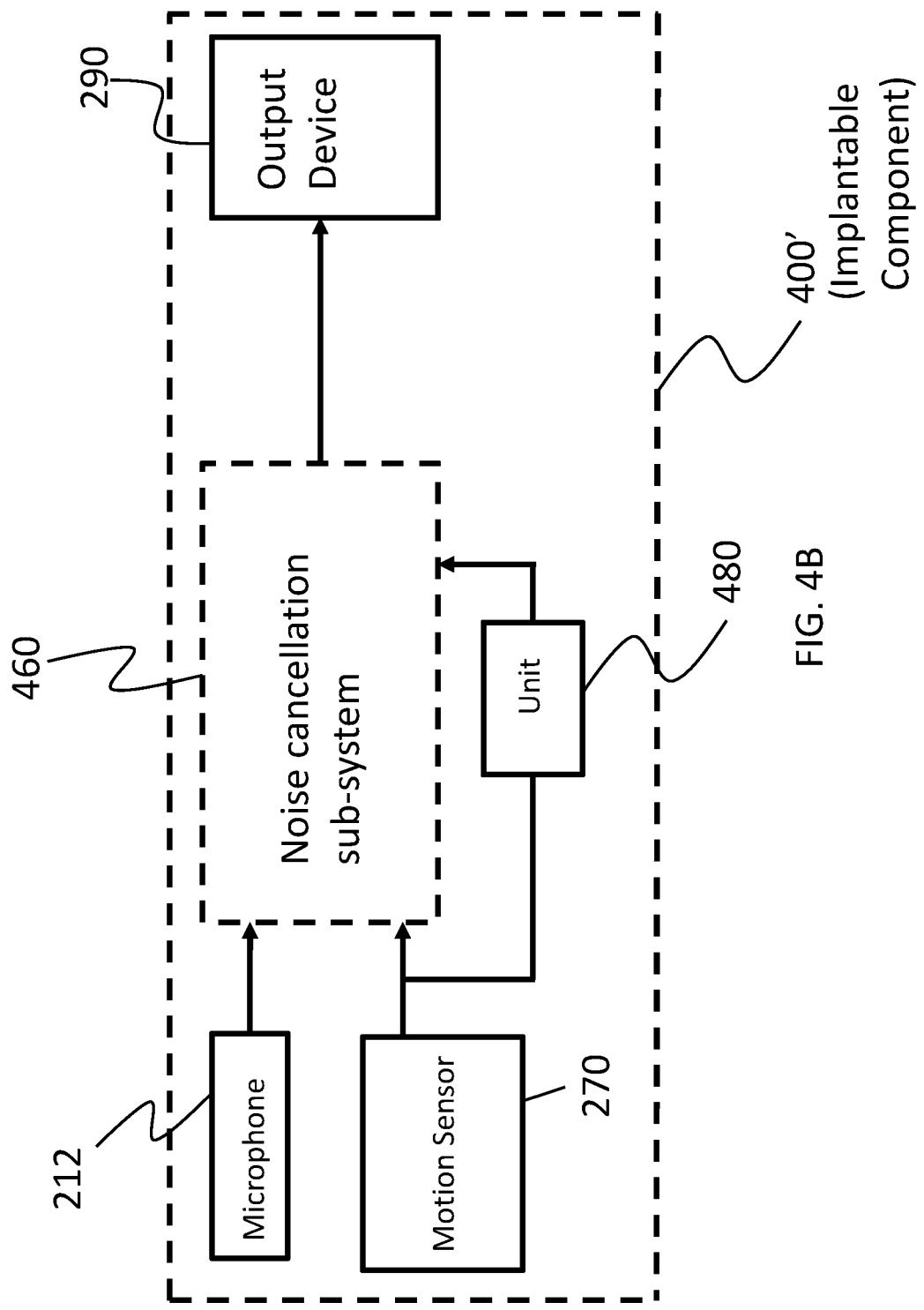
FIG. 4B is a schematic illustration of another exemplary embodiment utilizing a reference signal to identify impulsive noises according to an exemplary embodiment.

Thus, FIGS. 4A and 4B present an exemplary embodiment of a microphone system (e.g., all elements of the implantable component 400 other than the output device 290) that comprises two separate sensors (microphone 212 and motion sensor 270). One of the sensors (microphone 212) is configured to output a first signal (e.g., an audio signal) based on an ambient sound relative to a recipient of the system. The other of the sensors (motion sensor 270) is configured to output a second signal corresponding to a noise reference. In an exemplary embodiment, this signal includes a body conducted body noise component. The microphone system includes signal processing circuitry configured to process the first signal based on the second signal and output a third signal (e.g., an audio signal) based on the processed first signal, the third signal being the signal supplied to the output device 290. In an exemplary embodiment, the signal processing circuitry is configured to enhance the first signal by reference to the second signal and output the third signal based on the signal enhancement. By way of example only, such enhancement can be the noise cancellation noted above, using, for example, adaptive filters. Other signal enhancement can be implemented in other embodiments (alone or in addition to the aforementioned noise cancellation). Thus, an exemplary embodiment includes signal processing circuitry that affects the cancellation of body noise energy from the first signal. In an exemplary embodiment, this signal processing circuitry is circuitry of the noise cancellation sub-system 460.

Briefly, it is noted that the output signal of the motion sensor 270 is, with respect to scenarios involving impulsive energy resulting from internally generated noises (coughing, blowing nose, etc.) substantially entirely (including entirely) based on noise generated at a location or region within the recipient's body and conducted from there to the motion sensor through the body (e.g., by tissue). This is as contrasted to, e.g., an internal body noise that travels through the ambient environment (e.g. air) to impinge upon the skin, causing pressure waves to travel through the skin to the motion sensor.

The output of motion sensor 270 serves as a reference signal. This signal is used to identify the presence and/or absence of impulsive noise. Additional details of this are described below.

The microphone system is configured to limit a broadband gain of the third signal based on a feature of the second signal (the reference signal). In an exemplary embodiment, the feature is the presence of impulsive energy, including broadband impulsive energy, in the second signal, and the unit 480 is configured to identify the presence of such in the output from motion sensor 270. Accordingly, in an exemplary embodiment, the microphone system includes additional signal processing circuitry separate from the aforementioned signal processing circuitry (e.g., the circuitry affecting the noise cancellation). This additional circuitry is configured to limit the broadband gain of the third signal based on the presence of impulsive energy in the second signal. In an exemplary embodiment, this circuitry can be part of unit 480, and can extend to include circuitry that is part of unit 482.

It is noted that while the various circuitries are separate, the circuitries can be part of the same processor and/or the same unit. That is, while the functional schematics of FIGS. 4A and 4B depict separate units and sub-units, the units and sub-units can be part of the same component, where the different signal paths are processed by different circuits of the same unit.

Briefly, it is noted that the third signal can be a processed first signal and/or can be a new signal based on the first signal. That is, in some embodiments, it can be utilitarian to process the signal from the microphone 212 utilizing sound processing techniques to achieve the noise cancellation and/or the broadband compression. In other embodiments, it can be utilitarian to generate a new signal (a third signal) that is based on the first signal (i.e., a signal generator can be present that receives control inputs based on the first and second signal that control the generator to output a third signal).

As noted above, exemplary embodiments can include configurations that apply broadband compression to the signal that will be used as a basis to control output device 290 in scenarios where the output from the motion sensor 270 includes impulsive energy. Some exemplary scenarios where the output signal from the motion sensor 270 can include impulsive energy include situations where the motion sensor receives vibrations corresponding to loud noises or the like. In some embodiments, the impulsive energy is a result of loud noises that originate within the body, such as, by way of example only and not by way of limitation, coughing, sneezing, blowing one's nose, eating, and laughing, where the loud body noises are conducted through tissue of the recipient to be received by motion sensor 270. In some embodiments, the impulsive energy is a result of contact with the body such as, tapping one's head, scratching one's body, stomping one's foot, clapping one's hands together, etc. Embodiments of the teachings detailed herein can be such that any body noise that is conducted through tissue of the recipient to the motion sensor 270 that results in energy of the signal output of the motion sensor 270 that is perceived as a loud noise by the recipient, even after noise cancellation via the sub-system 460, triggers unit 480 to apply broadband compression.

As just noted, embodiments herein apply broadband compression (or a frequency dependent compression) to the signal that is to be provided to output device 290, or, more generally, the signal that is to be the basis to control output device 290. This is because, in an exemplary embodiment, the aforementioned body noises that result in impulsive energy in the outputted signal from the motion sensor 270, are noises that have frequency content that is relatively broadband. That is, the energy is not generally limited to a narrow band of frequencies. By way of example only and not by way of limitation, the impulsive energy can have substantial content in frequencies from between 20 Hz to 20,000 kHz, although impulsive energy having substantial content in frequency ranges inside the aforementioned range can also be present. For example, the impulsive energy can have substantial content in frequencies from between 20 Hz to 100 Hz, 20 Hz to 1,000 Hz, 20 Hz to 3,000 Hz, 20 Hz to 5,000 Hz, or more.

Some additional details of the functionality of the unit 480 will now be described.

In an exemplary embodiment, unit 480 is configured to analyze the output of motion sensor 270 and determine an energy level of the output. In an exemplary embodiment, the unit is configured to determine the amplitude of the signal. Still further, in an exemplary embodiment, unit 480 is configured to evaluate whether or not the energy level of the signal from sensor 270 meets a given predetermined criteria. That is, in an exemplary embodiment, the determination as to whether to apply the compression is based on whether or not a reference signal meets a predetermined criteria. By way of example only and not by way of limitation, the unit 480 is configured to determine whether or not the energy level of the signal is above a predetermined value. Accordingly, in an exemplary embodiment, unit 480 can be configured such that it does not apply the broadband compression in most scenarios where the output signal of the motion sensor 270 is a result of tissue conducted own voice energy. In at least some embodiments, this can have utilitarian value in that in at least some instances, recipients desire to hear the sound of their own voice. That said, even when recipients do not desire to hear the sound of their own voice, the absence of the sound of their own voice can cause them to talk louder than would otherwise be appropriate.

Accordingly, in at least some embodiments, there is utilitarian value in the recipient hearing the sound of his or her own voice. Corollary to this is that there is utilitarian value in the recipient hearing his or her own voice in a manner such that gain applied thereto is not compressed, or at least not compressed in a manner different than that of other sounds. That is, while there is utilitarian value in applying broadband compression to some noises, there are other scenarios where there is not utilitarian value, or even where there is a deleterious effect to applying broadband compression to other noises (e.g., noises corresponding to those generated by tissue conducted own voice events). Thus, by a establishing a threshold value below which broadband compression is not applied, the utilitarian noises are provided to the recipient.

In at least some embodiments, the threshold energy level is based on a statistical analysis of a given population. As noted above, typically, own voice tissue conducted noises do not result in an output signal from a motion sensor above −23 dBFS. In this regard, −23 dBFS is a value that is just above normal own voice body conducted noise loudness. That said, this is simply a statistical value. Subjectively, some recipients may have a physiology such that the own voice tissue conducted noises result in an output signal from the motion sensor above −23 dBFS. Accordingly, in an exemplary embodiment, there is utilitarian value in customizing the unit 480 (e.g. fitting the unit) to a specific recipient. Accordingly, by way of example only and not by way of limitation, an exemplary embodiment can have a unit 480 configured to implement broadband compression upon a determination that an output signal from the motion sensor 270 includes impulsive energy at about (including exactly) −20, −21, −22, −23, −24, −25, −26 and/or −27 dBFS, or any value or range of values therebetween in 0.1 dBFS increments (e.g., −22.4 dBFS, −23.3 dBFS, −21.2 dBFS to about −24.7 dBFS).

As noted above, the energy level of the reference signal (output signal of sensor 270) can be used to identify the presence or absence of an impulse noise. That said, alternatively and/or in addition to this, other phenomena can be utilized to identify the presence or absence of an impulse noise. For example, the rise time of a broadband signal can be used to identify the presence of an impulse noise (even if the energy level is relatively low). For example, if a broadband signal appears with a rise time of tens of microseconds, it is a good indicator that the reference signal contains an impulse noise. In at least some embodiments, if a reference signal contains a broadband signal with a rise time of less than about 10, 20, 30, 40, 50, 60, 70, 80 and/or 90 microseconds or any value or range of values therebetween in 1 microsecond intervals, it is an indication that the reference signal contains an impulse noise (and thus the output of the microphone 212 contains an impulse noise).

In view of the above, at least some embodiments include a microphone system that is configured to automatically detect the presence of impulsive energy in the signal from the microphone 212 based on a reference signal (i.e., the signal from the motion sensor 270). Further, at least some exemplary embodiments are such that upon the automatic detection of the presence of impulsive energy in the signal from the motion sensor 270, the system automatically varies the broadband gain of the aforementioned third signal based on the detection of the presence of impulse energy. In this regard, it is noted that in at least some exemplary embodiments, irrespective of the presence or absence of impulse energy in the signal from motion sensor 270 (indeed, the signal path between the motion sensor 270 and the unit 480 could be completely severed and the teachings detailed herein can still be implemented in some embodiments), the microphone system applies gain to various frequency channels (the gain can vary from one channel to another, the gain can be applied to all channels equally, the gain might not be applied to some channels, but applied to others, etc.). In an exemplary embodiment, this gain can be applied before and/or after the noise-cancellation sub-system processes the output from the microphone 212. In an exemplary embodiment, upon the detection of the impulse energy presence in the signal from motion sensor 270, the amount of gain that is applied is limited across the entire frequency spectrum in some embodiments, across a substantial part of the entire frequency spectrum in some other embodiments, or across the majority of the frequency spectrum in some other embodiments, or across less than a majority of the frequency spectrum, relative to that which would be the case in the absence of the detection of the impulsive energy (e.g., in the absence of unit 480). In an exemplary embodiment, the system is configured to reduce the gain that is applied relative to that which would be the case in the absence of the impulsive energy in the signal from the motion sensor 270.

By way of example only and not by way of limitation, gain regimes utilized in some embodiments can be implemented by setting a knee-point at just above the normal own voice body conducted noise loudness (either statistical norm or subjective norm). In view of the above, in an exemplary embodiment, the knee-point can be set at one of the aforementioned dBFS values. In some embodiments, the gain applied above the knee-point is such that the output loudness increases linearly with increased input loudness, albeit at a different rate from that which was the case below the knee-point. Still further, in at least some embodiments, the gain applied above the knee-point can be constant irrespective of the increase in input loudness. In some other embodiments, the gain applied above the knee-point is such that the output loudness increases in a non-linear fashion with increasing input loudness (e.g., exponential growth by a factor between 0 and 1). Indeed, in some embodiments the gain applied above the knee-point can have multiple functions. For example, the gain applied above the knee-point in a first range immediately proximate the knee-point can be a linear function, the gain applied in a second range immediately proximate to the first range but on the other side thereof with respect to the knee-point, can be non-linear, and the gain applied in a third range immediately proximate to the second range but on the other side thereof with respect to the first range, can be constant. Any regime of varying the gain relative to that which would be the case in the absence of such upon a determination that the output of the motion sensor 270 contains energy levels according to the teachings detailed herein and/or variations thereof can be utilized in at least some embodiments, providing that the teachings detailed herein can be achieved.

Referring to FIG. 5, FIG. 5 depicts an exemplary functional schematic of an exemplary signal processing path separate from the signal processing path of the noise cancellation sub-system (at least until, in some embodiments, the paths are merged). More specifically, the signal path presented in FIG. 5 corresponds to the signal path that travels through the unit 480 of FIGS. 4A and 4B. Indeed, in an exemplary embodiment, FIG. 5 presents a unit 580 having the functionality of the unit 480 detailed above. Some exemplary features of this unit 580 will now be detailed.

Still with reference to FIG. 5, as can be seen, output from the motion sensor 270 is inputted into unit 584 (in addition to the signal processing system/noise cancellation system 460), which is a unit configured to evaluate the energy level associated with the output from the motion sensor 270. In an exemplary embodiment, unit 584 is a signal strength signal meter. For example, an IEC 61672-1 sound level meter can be used. In an exemplary embodiment, unit 584 includes circuitry configured to measure the energy level of the output of motion sensor 270. In an alternate embodiment, unit 584 estimates the energy level of the output of the motion sensor 270. In at least some embodiments, a root mean squares routine is utilized by unit 584 to obtain information indicative of the energy level of the output of the motion sensor 270. Any device, system, and/or method that can enable obtaining information indicative of the energy level of the output of motion sensor 270 can be utilized in at least some embodiments.

In at least some embodiments, unit 584 is configured with control circuitry to control the gain regime that will be applied as a result of the energy level of the output motion sensor 270. In an exemplary embodiment, unit 584 is configured to activate and/or deactivate compression unit 588 (the features of which are discussed in greater detail below) and/or adjust the operation of compression unit 588.

As can be seen in FIG. 5, the signal path represented therein further includes unit 586, which, in an exemplary embodiment, is a smoothing control unit. Unit 586 is configured to control smoothing characteristics of the gain compression to be applied to the signal outputted to the output device 290. Thus, in an exemplary embodiment, unit 586 controls compression unit 588 (again, the details of which are described below) to have given smoothing characteristics. In this regard, unit 586 includes control circuitry configured to control the smoothing characteristics. In an exemplary embodiment, unit 586 determines and/or otherwise receives (e.g., the unit 586 can be set based on certain parameters), attack and release parameters for the gain compression regimes. In an exemplary embodiment, the attack times and/or the release times are based on statistical preferences of a given population of the hearing prosthesis recipients. In some alternative embodiments, the attack times and/or the release times are based on a subjective preference of a given recipient. In some embodiments, the attack times and/or release times are controlled or otherwise governed based on the performance capabilities of the system (e.g., a sampling rate per second, etc.). In an exemplary embodiment, unit 586 controls the compressor 588 so that the attack times are about 1, 2, 3, 4, or 5 ms, or any value or range of values therebetween in about 0.1 ms increments. In an exemplary embodiment, unit 586 controls the release times to be about 15, 16, 17, 18, 19, 20, 21, 22, 23, 24 or 25 ms, or any value or range of value there is between about 0.1 ms increments. Smaller or larger values than those just detailed can be utilized in at least some embodiments. Indeed, in at least some embodiments, release times can potentially be between 40 to 80 ms (e.g., 50 to 70 ms). Any attack time and or release time that can enable the teachings detailed herein and/or variations thereof to be practiced can be utilized in at least some embodiments.

It is noted that in an exemplary embodiment, the hearing prosthesis 10 is configured so as to receive input that enables the attack and/or release times to be varied from device to device. In this regard, in an exemplary embodiment, the hearing prosthesis 10 can include an input unit configured to receive such input. In an exemplary embodiment, the recipient can adjust the attack and/or release times to suit his or her desires.

Continuing with reference to FIG. 5, unit 586 controls compressor 588. Compressor 588 is configured to apply compression, including broadband compression, to the gain applied to the signal provided to the output device 290. In an exemplary embodiment, the attack and/or release times of the compression applied by compressor 588 are controlled by the smoothing unit 586. Still further by way of example, the activation and or deactivation of the compressor is controlled by unit 584. Further, in at least some embodiments, unit 584 is configured to adjust the characteristics of the compressor (e.g., dynamically control the amount of compression to be implemented, etc.). In an exemplary embodiment, compressor 588 is a dedicated compressor of the hearing prosthesis. That is, by way of example only and not by way of limitation, in at least some embodiments, automatic gain control is utilized to control the gain of the output to the output device 290. By way of example only and not by way of limitation, in at least some embodiments where, for example, the hearing prosthesis is a cochlear implant, there is a multichannel syllabic compression automatic gain control feature that is utilized to control the loudness of the output. In at least some exemplary embodiments, this has utilitarian value with respect to addressing external speech loudness. In at least some embodiments having such syllabic compression, a separate compressor is utilized to achieve the teachings detailed herein with respect to body conducted noise. That said, in an alternate embodiment, a combined compressor can be utilized to achieve the syllabic compression and the broadband compression.

Collectively, units 584, 586 and 588 can be combined into a single unit 580. In an exemplary embodiment, unit 580 corresponds to unit 480 detailed above. That said, in an alternative embodiment, the units are separate.

In view of the above, it is noted that an exemplary embodiment includes a microphone system of a hearing prosthesis (and, in some embodiments, the entire hearing prosthesis), comprising an adaptive signal processing sub-system, such as by way of example, the adaptive noise cancellation sub-system discussed above. The microphone system further includes a gain compression sub-system configured to be reactive to body noise. The gain compression sub-system is independent of the adaptive signal processing sub-system and is configured to compress gain of the microphone system independently of the adaptive signal processing sub-system. In some embodiments, the gain compression sub-system is configured to compress gain of the microphone system independently of all other signal processing systems of the hearing prosthesis (the gain compression sub-system still utilizes output from the motion sensor to determine whether to compress gain of the microphone system).

Indeed, with respect to the gain compression sub-system being independent, it is noted that in at least some embodiments, the presence of impulse noise can be determined based entirely on the output of the motion sensor (i.e., without reference to the signal output by the microphone 212/only based on the signal from the motion sensor 270).

In at least some embodiments, the aforementioned adaptive signal processing sub-system includes an automatic gain control functionality that operates independently of the gain compression sub-system. By way of example only and not by way of limitation, this automatic gain control functionality is a syllabic compression automatic gain control functionality, such as may be the case in a cochlear implant as noted above.

As detailed above, in at least some embodiments, the attack time of the compressor unit 588 is relatively fast. Indeed, in at least some embodiments, the attack times are set as fast as it is possible to make such based on the underlying technology (e.g. which can be limited based on the sample speed of the microphone system). Conversely, the adaptive signal processing sub-system (e.g., the adaptive noise cancellation sub-system) is configured to react at a relatively slower speed. In this regard, in at least some exemplary embodiments, such is done to avoid clipping or the like. Accordingly, in an exemplary embodiment, the reaction time of the adaptive noise cancellation sub-system is slower than that of the gain compression sub-system. Indeed, by way of example only and not by way of limitation, attack times of the adaptive noise cancellation sub-system can be two, three, four, five, six, seven, eight, nine and/or 10 times longer than that of the gain compression sub-system.

In view of the above, it is noted that in an exemplary embodiment, the microphone system is configured such that the noise cancellation sub-system outputs a signal including a body noise component, if only due to the fact that the adaptive noise cancellation sub-system has a slower reaction time (i.e., the body noise component is present because the noise cancellation sub-system has not had time to react to fully cancel the body noise from the outputted signal). However, because the microphone system is configured such that the gain compression sub-system variably varies a gain of the signal depending on an energy level of body noise that resulted in the body noise component, the effect to the recipient of the body noise component that is included in the output of the adaptive noise cancellation sub-system is varied relative to that which would be the case in the absence of the gain compression sub-system that is independent of the noise cancellation sub-system (e.g., because the gain is reduced, it is not as loud).

Now with reference back to FIGS. 4A and 4B, the microphone system of the implantable component 400 can correspond to a subcutaneous microphone system. The system can be characterized as having two signal processing paths. The output from microphone 212 and motion sensor 270 (e.g., accelerometer) are inputs to one of the signal processing paths (a first signal processing path). As can be seen from the figures, that signal processing path can entail noise cancellation, such as by way of example only and not by way of limitation, body noise cancellation processing of the output of the microphone 212. Additionally, the output from the motion sensor 270 is an input to another of the signal processing paths (a second signal processing path). Concomitant with the teachings detailed above, in an exemplary embodiment, the subcutaneous microphone system is configured to vary broadband gain (or frequency dependent gain) applied to the first signal processing path based on an energy level of the output of the motion sensor 270. In an exemplary embodiment, the microphone system varies the gain upon a determination that the output of the motion sensor 270 has an energy level at and/or above a first threshold, the first threshold being any of those detailed above and or variations thereof or any other threshold that will enable the teachings detailed herein and/or variations thereof to be practiced.

More specifically, in an exemplary embodiment, the aforementioned microphone system is configured to apply a gain regime in the first signal processing path when the output of the motion sensor 270 has an energy level below a threshold, and apply a different gain regime in the first signal processing path when the output of the motion sensor 270 has an energy level above a threshold. (It is noted that the just utilized language does not address the issue of what occurs when the energy level is at a threshold—in some embodiments, if the energy level is at the threshold, the former gain regime is applied, and in other embodiments, if the energy level is at the threshold, the latter gain regime is applied.) In this regard, the latter gain regime is a gain regime that applies a lower gain in the first signal path relative to that which is the case with the former gain regime.

A method of utilizing an exemplary hearing prosthesis having an exemplary microphone system will now be described. In general terms, the exemplary method is directed towards a scenario spanning two different temporal periods in which body conducted body noises are received by an implanted microphone system, the body conducted body noises received by the implanted microphone having different energy levels. Based on the energy levels, the operation of the microphone system is varied from one of the temporal periods relative to the other of the temporal periods.

Figure 6:
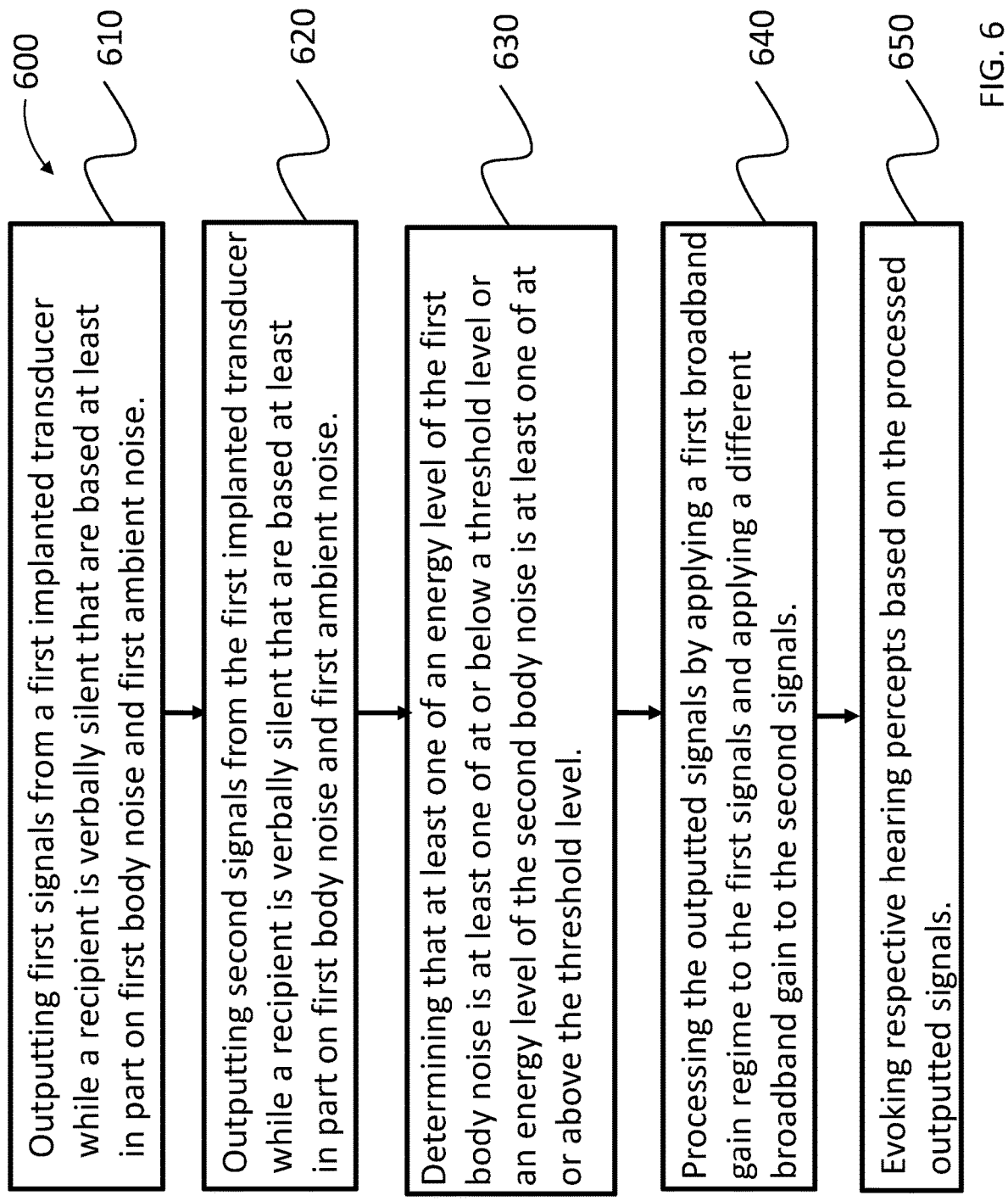
FIG. 6 presents a flowchart for an exemplary method according to an exemplary embodiment.

More specifically, FIG. 6 depicts a flowchart for an exemplary method 600 according to an exemplary embodiment. Method 600 includes method action 610, which entails outputting first signals from a first implanted transducer (e.g., the microphone 212) while a recipient is verbally silent (not talking) that are based at least in part on first body noise and first ambient noise, both of which are conducted through tissue of the recipient to the transducer. In an exemplary embodiment, method action 610 occurs during a first temporal period in which the internal body noises are relatively soft (e.g., grumbling stomach noises) and a person is speaking to the recipient (the source of the first ambient noise). By way of example only and not by way of limitation, in a scenario implementing the microphone systems detailed above, the first body noise is body noise that results in an output of the motion sensor 270 that is below −23 dBFS.

Method 600 further includes method action 620, which entails outputting second signals from the first implanted transducer, also while the recipient thereof is verbally silent. These outputted signals are based at least in part on second body noise and second ambient noise, both of which are conducted through tissue of the recipient to the first implanted transducer. Again, in an exemplary embodiment, the ambient noises are generated by a speaker speaking to the recipient. In an exemplary embodiment, method action 610 is executed during a first part of the speaker's sentence, and method action 620 is executed during a second, later part, of the speaker's sentence. In an exemplary embodiment, the second body noise that is conducted through tissue of the recipient to the first implanted transducer is body noise that results in the motion sensor 270 outputting a signal having energy above that which was the case for the first signal (e.g., above −23 dBFS). By way of example only and not by way of limitation, the second body noise can result, at least in part, from at least one of coughing, nose blowing, eating or laughing of the recipient, or the recipient stomping his or her foot.

Method 600 also includes method action 630. This entails evaluating the energy level of the body noises and making a determination about the energy level of at least one of the body noises. By way of example only and not by way of limitation, during method action 630, a determination can be made that the energy level of the first body noise is at and/or below a threshold level. Such can be accomplished, for example, by analyzing the output of motion sensor 270 and determining whether the output is at and/or below −23 dBFS. Such can also be accomplished, for example, by analyzing the output of the motion sensor 270 and determining whether the output is at and/or above −23 dBFS.

It is noted that the action of determining that an energy level is below a threshold level includes a determination that the energy level is not above the threshold level. That is, the determination of the negative implies the positive, and thus the positive is determined. In the same vein, it is noted that the action of determining that the energy level is above a threshold level includes a determination that the energy level is not below the threshold level.

It is noted that while method action 630 is presented after method action 620, in an alternate embodiment, method action 630 can be practiced in between method action 610 and method action 620. Alternatively, in an exemplary embodiment, method action 630 can be practiced in part between method actions 610 and 620, and in part after method action 620. Any order of practicing the method actions detailed herein and/or variations thereof that can have utilitarian value can utilize in at least some embodiments.

After method action 630 is executed, method action 640 is executed, which entails processing the outputted signals that are outputted by the first implanted transducer. In an exemplary embodiment, this entails applying a first gain regime to the first signals and applying a second gain regime to the second signals different from the first gain regime. In an exemplary embodiment, the second gain regime is compressed above the threshold level relative to the first gain regime, in accordance, for example, with the teachings above (e.g., by utilizing the compressor noted above, which can be independent of other automatic gain control systems of the hearing prosthesis). By way of example only and not by way of limitation, for the purposes of conceptual illustration, the first gain regime can be a 1 to 1 (power out vs. power in) gain regime, and the second gain regime can be a 0.5 to 1 (again, power out vs. power in) gain regime. Alternatively, again for the purposes of conceptual illustration, the first gain regime can be a 2 to 1 gain regime and the second gain regime can be a 1.5 to 1 gain regime. Still further, the first gain regime can be a 1 to 1 gain regime and the second gain regime can be a −1 to 1 gain regime, or a 0 to 1 gain regime, etc. Any gain regime of the first and/or second gain regime that will enable the teachings detailed herein and/or variations thereof to be practiced can be used to enable at least some embodiments.

It is noted that in at least some exemplary embodiments of method action 640, the second gain regime is applied for a temporal period that at least partially overlaps a temporal period in which the second body noise is present. Corollary to this is that in such embodiments, the second gain regime is applied for a temporal period that at least partially overlaps a temporal period in which the energy level of the second signals is above that which was the case for the first signal (e.g., above −23 dBFS). In some exemplary embodiments, the temporal period of second gain regime application is such that it begins at the time that it is determined that the energy level of the second signal is above that which was the case for the first signal and ends at the time that it is determined that the energy level of the second signal is no longer above that which was the case for the first signal (or the time that it is not determined that the energy level of the second signal is above that which was the case for the first signal) or the time that the energy level is determined to meet some other criteria, etc. That said, in some alternative embodiments, the temporal period of second gain regime application can extend past a time that it is determined that the energy level of the second signal is no longer above that which was the case for the first signal (or meets some other criteria). It is further noted that in some alternate embodiments, the temporal period of second gain regime application can extend for a set period. Proximate the end of the set period (which includes at the end of the predetermined period), the energy level of the second signal can be reevaluated, and if the energy level is above that which was the case for the first signal, the temporal period can be extended for another set period.

It is noted that the aforementioned set period(s) can be variable in length. For example, in some embodiments, depending on the energy levels of the various signals, the period can be different for different energy levels.

Still further, by way of example only, the temporal period of second gain regime application can be a predetermined period that is triggered upon the determination of the requisite energy level, and is restarted at every instance of the determination of the requisite energy level (or some other phenomenon). For example, if the energy levels are evaluated every 20 ms, the temporal period could be 50 ms, and thus an evaluation (reevaluation) of the energy level would occur with 30 ms more to go in the temporal period. Upon a determination that the requisite energy level is present, the temporal period would be reset. In at least some embodiment where the evaluation cycle time is such that there are two or more evaluations in a given temporal period, this can have utilitarian value in that a single "false negative" would not interrupt the application of the second gain regime.

Method 600 also includes method 650, which entails evoking respective hearing percepts based on the processed output signals.

As stated above, method actions 610 and 620 are executed while the recipient is verbally silent. That said, because at least some embodiments are keyed to a normal own voice level body conducted noise so as to improve the likelihood that the recipient will be able to hear himself or herself, the aforementioned threshold levels correspond to an energy level that is relative to a normal own voice level, such as, for example, a non-shouting own-voice body noise energy level of the recipient (e.g., that which results from the recipient speaking normally). By way of example only and not by way of limitation, the threshold level corresponds to an energy level at or below a non-shouting own-voice body noise energy level. Still further by way of example only and not by way of limitation, the threshold level can correspond to a level that, in statistical terms, the recipient can hear own voice body conducted noises for a substantial majority of the time (e.g., 95%, 99% of the time, etc.). In this regard, statistically speaking, the recipient will only very rarely talk loudly. Accordingly, in an exemplary embodiment, the threshold can be set to cover the vast majority of speaking modes of the recipient. Again, in at least some embodiments, it is noted that the hearing prostheses detailed herein are customized to the particular recipient. Accordingly, method 600 can be executed in a manner that is subjective to a given recipient.

As noted above, the compression sub-systems detailed herein can operate independently of the noise cancellation sub-systems. Accordingly, in an exemplary embodiment of method 600, the method further includes determining that a non-own-voice impulsive body conducted noise phenomenon has commenced based at least in part on the determination of the energy level of the second body noise (i.e., the body noise occurring when the second signal was outputted from the implanted transducer). Corollary to this is that method 600 also can include adjusting the processing of the outputted signals (from the first implanted transducer), from that which was the case prior to the determination of the commencement of the non-own-voice impulsive body conducted noise phenomenon, based on the determination of the commencement of the non-own-voice impulsive body conducted noise phenomenon such that the gain applied in the second gain regime is different than that applied in the first gain regime. It is noted that in embodiments where the second gain regime is a compressive gain regime, the gain applied to the second signals can still result in a signal amplitude that is higher than that of the first signals which results from the gain applied in the first gain regime to those first signals—the resulting amplitude is just not as high as would have been the case if the non-own voice impulsive body conducted noise was not an impulsive.

Again, it is noted that in at least some embodiments, the gain regime is a broadband gain regime, while in other embodiments, the gain regime is a frequency dependent gain regime.

Consistent with the teachings detailed above, in an exemplary embodiment, the aforementioned action of determining a non-own-voice impulsive body conducted noise phenomenon has commenced includes analyzing energy levels from signals from a second implanted transducer that is isolated from the ambient noises and determining that a non-own-voice impulsive body conducted noise phenomenon has commenced.

Figure 7:
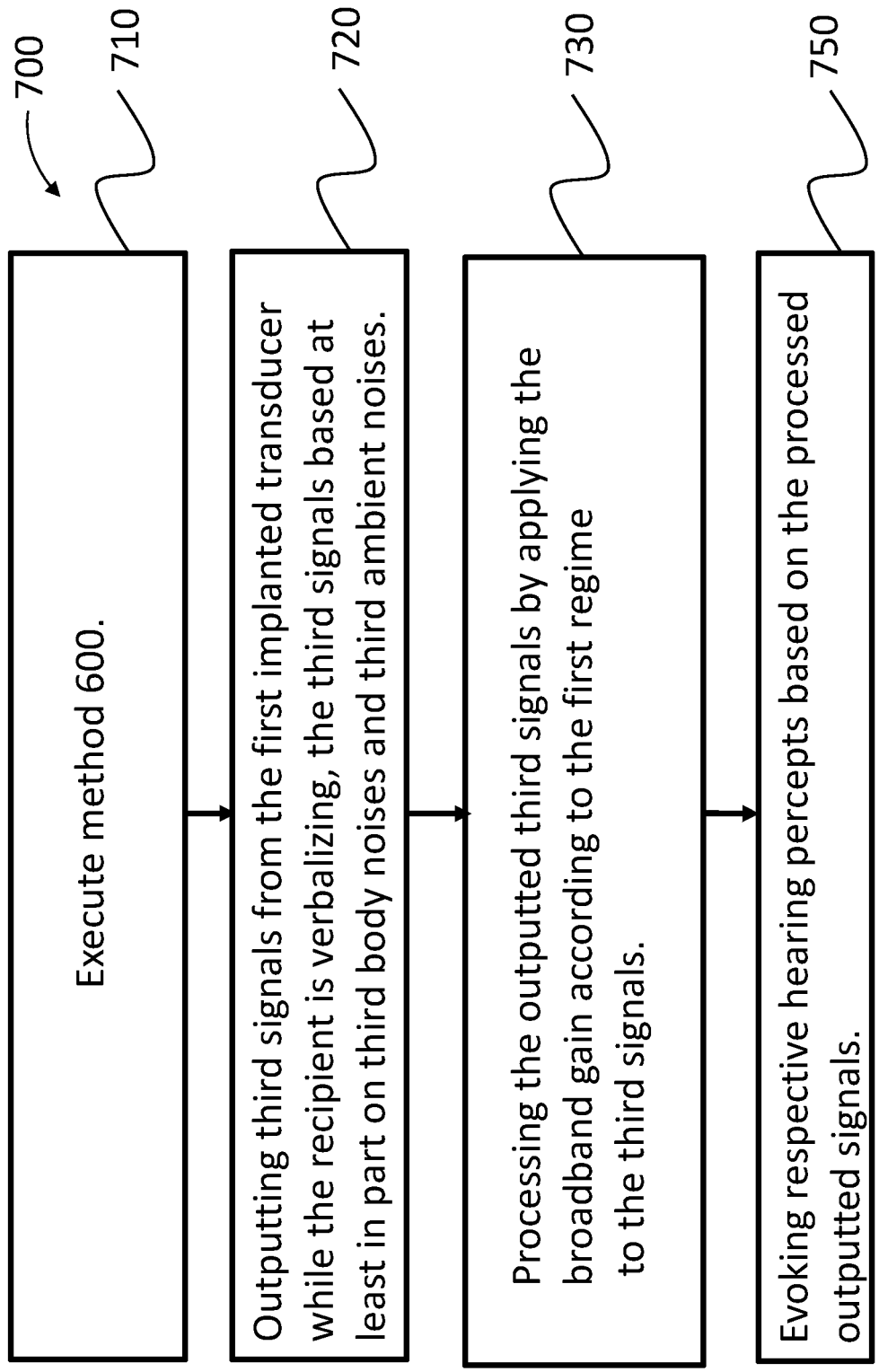
FIG. 7 presents another flowchart for an exemplary method according to an exemplary embodiment.

FIG. 7 presents an alternate exemplary method. Method 700 is directed towards passing the own-voice body conducted noise to the recipient, at least those that do not constitute impulsive own-voice body conducted noise, using non-compressed gain (or, in the parlance of method 600, according to the first regime). To this end, method 700 includes method action 710, entailing executing method 600. Method 700 also includes method action 720, which entails outputting third signals from the first implanted transducer while the recipient is verbalizing. These third signals are based at least in part on third body noises and third ambient noises occurring after the first and second body noises and first and second ambient noises. The third body noises and third ambient noise are conducted through tissue to the first transducer (microphone 212). The third body noises include at least in part own-voice body noise. This is followed by method action 730, which entails processing the outputted third signals by applying the non-reduced gain to the third signals, and method action 740, which entails evoking respective hearing percepts based on the processed outputted third signals.

As detailed above, most of the description is directed towards broadband gain regimes to address broadband impulse noises. However, alternate embodiments utilize frequency dependent gain regimes with frequency specific impulse noises. Accordingly, any description herein with respect to broadband gain regimes and broadband impulse noises corresponds to an alternate description of a frequency dependent gain regime for use with frequency specific impulse noises.

It is noted that any method detailed herein also corresponds to a disclosure of a device and/or system configured to execute one or more or all of the method actions associated therewith detailed herein. In an exemplary embodiment, this device and/or system is configured to execute one or more or all of the method actions in an automated fashion.

It is noted that embodiments include non-transitory computer-readable media having recorded thereon, a computer program for executing one or more or any of the method actions detailed herein. Indeed, in an exemplary embodiment, there is a non-transitory computer-readable media having recorded thereon, a computer program for executing at least some of the method actions detailed herein, the computer program including code for such.

It is further noted that any device and/or system detailed herein also corresponds to a disclosure of a method of operating that device and/or using that device. Furthermore, any device and/or system detailed herein also corresponds to a disclosure of manufacturing or otherwise providing that device and/or system.

While various embodiments of the present invention have been described above, it should be understood that they have been presented by way of example only, and not limitation.

It will be apparent to persons skilled in the relevant art that various changes in form and detail can be made therein without departing from the spirit and scope of the invention.

What is claimed is:

1. A microphone system, comprising:
a first sensor configured to output a first signal based on an ambient sound relative to a recipient of the system;
a second sensor configured to output a second signal corresponding to a noise reference; and
first signal processing circuitry configured to process the first signal based on the second signal and output a third signal based on the processed first signal, wherein
the system is configured to limit a gain of the third signal based on the presence of impulsive energy in the second signal.

2. The microphone system of claim 1, wherein:
the first and second sensors are implantable sensors; and
the microphone system is configured such that the second sensor is substantially isolated from energy resulting from the ambient sound upon which the first signal is based.

3. The microphone system of claim 1, wherein:
the microphone system is configured such that the second signal outputted by the second sensor is based substantially entirely on noise generated at a location or region within the recipient's body and conducted from there to the second sensor through the body.

4. The microphone system of claim 1, wherein:
the first signal processing circuitry is configured to enhance the first signal by reference to the second signal and output the third signal based on the signal enhancement.

5. The microphone system of claim 1, wherein
the system is configured to detect a presence of an impulse energy in the second signal and automatically limit the gain of the third signal based on the detection of the impulse energy presence.

6. The microphone system of claim 1, wherein
the system is configured to reduce a gain of the third signal relative to that which would be the case in the absence of impulsive energy in the second signal.

7. The microphone system of claim 1, wherein
the system is configured, based on the absence of impulsive energy in the second signal, to apply a gain of the third signal that is higher than that of the limited gain that would be applied based on the presence of the impulsive energy in the second signal.

8. The microphone system of claim 1, wherein
the system is configured to reduce a gain of the third signal relative to that which would be the case in the presence of impulsive energy in the second signal.

9. The microphone system of claim 1, wherein
the system is configured to apply the same gain to the third signal relative to that which would be the case in the absence of an impulsive energy in the second signal.

10. The microphone system of claim 1, wherein:
the microphone system includes means for limiting gain of the third signal based on the presence of impulsive energy in the second signal.

11. A subcutaneous microphone system, comprising:
a first implantable transducer configured to transduce energy from an ambient signal and body noise;
a second implantable transducer configured to transduce energy from body noise;
a first signal processing path; and
a second signal processing path, wherein an output of the first implantable transducer and an output of the second implantable transducer are inputs to the first signal processing path,
the output of the second implantable transducer is an input to the second signal processing path, and
the microphone system is configured to vary gain applied to the first signal processing path based on a characteristic of a signal of the second signal processing path.

12. The subcutaneous microphone system of claim 11, wherein:
the microphone system is configured to vary the gain applied to the first signal processing path (i) when an output of the second implantable transducer has an impulsive energy level at least one of at or above a first threshold or (ii) in response to the output of the second implantable transducer having had an impulsive energy level at least one of at or above a first threshold.

13. The subcutaneous microphone system of claim 11, wherein the first signal processing path includes body noise cancellation processing of the output of the first transducer.

14. The subcutaneous microphone system of claim 11, wherein the signal of the second signal processing path is based on an output of a device different than the second implantable transducer and based on a characteristic of an output of the second implantable transducer as opposed to being the output of the second implantable transducer.

15. The subcutaneous microphone system of claim 14, wherein the characteristic is an energy level of the output of the second implantable transducer.

16. The subcutaneous microphone system of claim 11, wherein:
the microphone system includes means for varying gain applied to the first signal processing path based on a characteristic of a signal of the second signal processing path.

17. The subcutaneous microphone system of claim 11, wherein:
the microphone system is configured to maintain the gain applied to the first signal processing path (i) when an output of the second implantable transducer has an impulsive energy level below a first threshold or (ii) in response to the output of the second implantable transducer having had an impulsive energy level below a first threshold.

18. The subcutaneous microphone system of claim 11, wherein the first signal processing path includes body noise cancellation processing of the output of the first transducer, which cancellation occur, with respect to signal travel, prior to where the system is configured to vary gain applied to the first signal processing path based on a characteristic of the signal of the second signal processing path.

19. The subcutaneous microphone system of claim 11, wherein the second signal processing path is completely isolated from the first signal processing path.

20. The subcutaneous microphone system of claim 11, wherein the microphone system is configured to cancel body noise from output of the first implantable transducer using output from the second implantable transducer separately and distinctly from varying gain applied to the first signal processing path based on the characteristic of the signal of the second signal processing path.

21. The subcutaneous microphone system of claim 11, wherein the microphone system is configured to cancel body noise from output of the first implantable transducer using output from the second implantable transducer prior to varying gain applied to the first signal processing path based on the characteristic of the signal of the second signal processing path such that the varied gain applied to the first signal processing path is applied to a signal from which body noise has been cancelled.

22. The subcutaneous microphone system of claim 11, wherein:
   the microphone system is configured to automatically maintain the gain applied to the first signal processing path (i) when an output of the second implantable transducer has an impulsive energy level below a first threshold or (ii) in response to the output of the second implantable transducer having had an impulsive energy level below a first threshold.

23. A method, comprising:
   outputting first signals at a first location within a recipient, while the recipient is verbally silent, that are based at least in part on first body noise and first ambient noise, both of which are conducted through tissue of the recipient;
   subsequently outputting second signals at the first location within the recipient, while the recipient is verbally silent, that are based at least in part on second body noise and second ambient noise, both of which are conducted through tissue of the recipient;
   determining that an impulsive energy level of the first body noise is at least one of at or below a threshold level or that an impulsive energy level of the second body noise is at least one of at or above the threshold level;
   processing the outputted signals by applying a first broadband gain regime to the first signals and applying a second broadband gain regime to the second signals different from the first broadband gain regime; and
   evoking respective hearing percepts based on the processed outputted signals.

24. The method of claim 23, wherein:
   the first signals and second signals are outputted from a first implanted transducer; and
   the method further comprises:
      while outputting the first signals, outputting third signals from a second implanted transducer that are based at least substantially entirely on the first body noise which is conducted through tissue of the recipient to the second implanted transducer; and
      while outputting the second signals, outputting fourth signals from the second implanted transducer that are based at least substantially entirely on the second body noise which is conducted through tissue of the recipient to the second implanted transducer, wherein
   the action of determining that an impulsive energy level of the first body noise is at least one of at or below a threshold level or that an impulsive energy level of the second body noise is at least one of at or above the threshold level is based on at least one of the third signals or the fourth signals.

25. The method of claim 23, wherein:
the second broadband gain regime is compressed above the threshold level relative to the first broadband gain regime.

26. The method of claim 25, further comprising:
determining that a non-own-voice impulsive body conducted noise phenomenon has commenced based at least in part on the determination of the energy level of the second body noise; and
adjusting the processing of the outputted signals from that which was the case prior to the determination of the commencement of the non-own-voice impulsive body conducted noise phenomenon based on the determination of the commencement of the non-own-voice impulsive body conducted noise phenomenon such that the gain applied in the second broadband gain regime is higher than that applied in the first broadband gain regime.

27. The method of claim 23, wherein:
the threshold level corresponds to an energy level at or below a non-shouting own-voice body noise energy level of the recipient.

\* \* \* \* \*